(12) United States Patent
Chang et al.

(10) Patent No.: US 9,474,735 B2
(45) Date of Patent: Oct. 25, 2016

(54) LIVER FUNCTION IMPROVEMENT AND TREATMENT OF LIVER DISEASE

(71) Applicant: Industrial Technology Research Institute, Hsin Chu (TW)

(72) Inventors: Shau-Feng Chang, Hsinchu (TW); Chun-Hsien Ma, Hsinchu (TW); Kuo-Yi Yang, Hsinchu (TW); Chien-Tung Lin, Hsinchu (TW); Shyh-Horng Lin, Hsinchu (TW); Kai-Wen Huang, Taipei (TW)

(73) Assignee: Industrial Technology Research Institute (ITRI), Hsin Chu (TW)

( * ) Notice: Subject to any disclaimer, the term of this patent is extended or adjusted under 35 U.S.C. 154(b) by 0 days.

(21) Appl. No.: 14/574,036

(22) Filed: Dec. 17, 2014

(65) Prior Publication Data

US 2015/0133539 A1    May 14, 2015

Related U.S. Application Data

(62) Division of application No. 12/908,185, filed on Oct. 20, 2010, now abandoned.

(30) Foreign Application Priority Data

Dec. 30, 2009 (TW) .............................. 98145737 A

(51) Int. Cl.
| | | |
|---|---|---|
| *A61K 31/353* | (2006.01) | |
| *A61K 31/70* | (2006.01) | |
| *A61K 31/765* | (2006.01) | |
| *A61K 31/352* | (2006.01) | |

(52) U.S. Cl.
CPC .......... *A61K 31/353* (2013.01); *A61K 31/352* (2013.01); *A61K 31/70* (2013.01); *A61K 31/765* (2013.01)

(58) Field of Classification Search
CPC .. A61K 31/353; A61K 31/765; A61K 31/70; A61K 31/352
See application file for complete search history.

(56) References Cited

U.S. PATENT DOCUMENTS

| | | |
|---|---|---|
| 5,760,010 A | 6/1998 | Klein |
| 7,371,776 B2 | 5/2008 | Ramljak et al. |
| 2003/0104079 A1* | 6/2003 | Sakanaka ................ C07J 17/00 424/728 |
| 2005/0142222 A1 | 6/2005 | Pan et al. |
| 2010/0055065 A1 | 3/2010 | Takeshita et al. |
| 2010/0168221 A1 | 7/2010 | Lee et al. |
| 2013/0123204 A1 | 5/2013 | Lee et al. |

FOREIGN PATENT DOCUMENTS

| | | |
|---|---|---|
| CN | 1443533 | 9/2003 |
| CN | 1933818 | 3/2007 |
| CN | 101822372 | 9/2010 |
| JP | 2009242374 | 10/2009 |

OTHER PUBLICATIONS

Chang, et al.,"The Anti-Hepatitis B Virus Activity of Boehmeria nivea Extract in HBV-viremia SCID Mice", eCAM2010; 7 (2) 189-195, Advance Access Publication Jan. 7, 2008.
Czochanska, et al., "Polymeric proanthocyanidins. Stereochemistry, structural unites, and molecular weight", Journal of the Chemical Society, 1980, (10), 2278-2286.
Sugimoto, et al., (J Hepatobiliary Pancreat Surg 2006: 13: 543-548).

* cited by examiner

*Primary Examiner* — Aradhana Sasan
(74) *Attorney, Agent, or Firm* — Cesari and McKenna LLP

(57) ABSTRACT

A pharmaceutical preparation containing polymeric compounds as shown in the specification. This preparation can be used to improve liver function and treat liver disease, and promoting liver tissue regeneration.

11 Claims, No Drawings

LIVER FUNCTION IMPROVEMENT AND TREATMENT OF LIVER DISEASE

CROSS-REFERENCE TO RELATED APPLICATIONS

This is a division of U.S. patent application Ser. No. 12/908,185, filed on Oct. 20, 2010 which claims the benefit of Taiwanese Application No. 98145737, filed on Dec. 30, 2009. The contents of the prior application are hereby incorporated herein by reference in their entirety.

BACKGROUND

The liver, a vital organ, plays a major role in metabolism of breaking down or modifying toxic substances. It also performs other important function, e.g., glycogen storage, hormone production, plasma protein synthesis, and red blood cell decomposition.

Life-threatening liver conditions include liver fibrosis, liver cirrhosis, liver inflammation, liver viral infection, and liver cancer.

There is an urgent need in enhancing liver function and treating liver conditions.

SUMMARY

One aspect of this invention relates to a method of improving liver function by administering to a subject in need thereof a pharmaceutical composition obtained by mixing a pharmaceutically acceptable carrier and an isolated preparation containing 20% or higher by weight one or more polymeric compounds each derived from two or more monomer units having Formula (I):

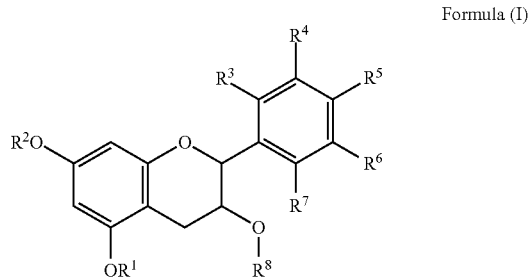

Formula (I)

wherein each of $R^1$ and $R^2$, independently, is H, alkyl, or acyl; each of $R^3$, $R^4$, $R^5$, $R^6$, and $R^7$, independently, is H, OH, alkoxyl, or acyl; and $R^8$ is H or a saccharide moiety.

Referring to the above formula, the monomer units in the polymeric compound may have one or more of the following features: $R^1$ and $R^2$, independently, is H, each of $R^3$ and $R^7$ is H, and each of $R^4$, $R^5$, and $R^6$ is OH or alkoxyl, and $R^8$ is H.

In the polymeric compounds, monomer units may be covalently linked to each other via bonding between any two atoms of different monomer units, e.g., C4-C8 bonding (i.e., bonding formed between the C4 carbon of one monomer unit and the C8 carbon of the other monomer unit), C4-C6 bonding (i.e., bonding formed between the C4 carbon of one monomer unit and the C6 carbon of the other monomer unit), or C2-O7 (i.e., bonding formed between the C2 carbon of one monomer unit and the O7 oxygen of the other monomer unit). In one example, all of the monomer units are covalently bonded to each other via C4-C8 bonding. In another example, all of the monomer unites are covalently bonded to each other via C4-C6 bonding. Of note, the numbering of atoms of a cyclic compound is well commonly used in chemical nomenclatures. Shown below is the numbering of the atoms of the core structure of the polymeric compounds of Formula (I):

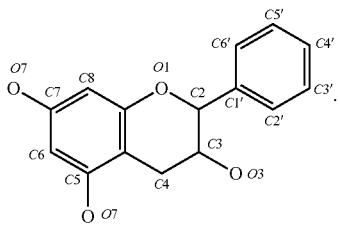

The "isolated preparation" refers to a composition containing one or more of the above-described polymeric compounds that has been partitioned from the natural source or the synthesis mixture.

The term "alkyl" refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "acyl" refers to a —C(O)-alkyl or —C(O)-aryl radical. Examples of acyl groups include, but are not limited to, —C(O)—CH₃ and —C(O)-ph. The term "alkoxy" refers to an —O-alkyl radical. Examples of alkoxy groups include, but are not limited to, —OCH₃ and —OCH₂CH₃.

Alkyl mentioned herein can be either substituted or unsubstituted. Examples of a substituent include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl are optionally further substituted with alkyl, aryl, heteroaryl, halogen, hydroxyl, amino, mercapto, cyano, or nitro.

The term "saccharide moiety" refers to a carbohydrate radical. It can be a radical of monosaccharide (e.g., allose, altrose, glucose, mannose, gulose, idose, galactose, talose, ribuose, psicose, fructose, sorbose, or tagatose), disaccharide (e.g., sucrose, lactulose, lactose, maltose, trehalose, or cellobiose), oligosaccharide (containing 3-10 monosaccharides), or polysaccharide (containing more than 10 monosaccharides).

The polymeric compounds described above include the compounds themselves, as well as their salts, prodrugs, and solvates, if applicable. A salt, for example, can be formed between an anion and a positively charged group (e.g., ammonium ion) on a polymeric compound. Suitable anions include chloride, bromide, iodide, sulfate, nitrate, phosphate, citrate, methanesulfonate, trifluoroacetate, acetate, succinate, malate, tosylate, tartrate, fumurate, glutamate, glucuronate, lactate, glutarate, and maleate. Likewise, a salt can also be formed between a cation and a negatively charged group (e.g., phenolate or carboxylate) on a polymeric compound. Suitable cations include sodium ion, potassium ion, magnesium ion, calcium ion, and an ammonium cation. The compounds may also be in prodrug and solvate form. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

The polymeric compounds contain asymmetric centers. Thus, they can occur as racemates and racemic mixtures, single enantiomers, individual diastereomers, and diastereomeric mixtures. Such isomeric forms are contemplated.

Another aspect of this invention relates to a method of treating liver disease or promoting regeneration of liver tissues by administering to a subject in need thereof a pharmaceutical composition obtained by mixing a pharmaceutically acceptable carrier and the isolated preparation described above.

Also within the scope of this invention is use of the isolated preparation described above for improving liver function/treating liver disease/promoting regeneration of liver tissues or for the manufacture of a medicament in the above-mentioned improvement/treatment/promotion.

The details of many embodiments of the invention are set forth in the description below. Other features, objects, and advantages of the invention will be apparent from the description and the claims.

DETAILED DESCRIPTION

Certain polymeric compounds of Formula (I) described above can be obtained from natural sources. For example, certain compounds can be extracted from roots, stems, and leaves of Ericacea (e.g., *Boehmeria nivea*), Rosaceae, Pinaceae, Vitaceae, or Urticaceae as follows:

Dry roots, stems, or leaves of the plant are immersed in water, an organic solvent, a mixture of water and an organic solvent, or a mixture of two or more organic solvents for a predetermined period of time to ensure that a sufficient amount of the desired compound is dissolved. Examples of organic solvents include, but are not limited to, methanol, ethanol, propanol, acetone, ethyl acetate, chloroform, dichloromethane, and dimethyl sulfoxide.

The above operation can take place at room temperature. Alternatively, it can be performed at elevated temperature. For example, the extracting solvent is refluxed for a certain period to facilitate extracting the desired ingredients from the plant parts.

To promote the stability or solubility of the desired ingredients, one can add inorganic acid (e.g., HCl), organic acid (e.g., ascorbic acid or tartaric acid), inorganic base (e.g., $Na_2CO_3$ or NaOH), organic base (e.g., triethylamine), or a buffer agent (e.g., $NaH_2PO_4$ or triethylamine hydrochloride). NaCl or other salts may be also added to increase the polarity of the extracting solvent.

The immersing time varies. It can be 2 hours to 7 days, depending on the extracting solvent and temperature. After the immersing, the solvent is separated from the plant parts and concentrated. The thus-obtained crude extract is further purified.

One can rinse the crude extract to remove certain impurities. For example, the crude product is first dissolved in polar solvent, such as alcohol, water, or a mixture thereof, the resulting solution is then rinsing with an apolor solvent, e.g., n-hexane, to remove lipid or other apolor substances or rinsing with chloroform or ethyl acetate to remove small phenol compounds, and finally the rinsed solution is concentrated to dryness to afford a partially purified product for use in the above-mentioned treatment.

One can also use chromatography to remove impurities. Chromatography technologies include paper chromatography, thin layer chromatography, column chromatography, gas chorography, and liquid chromatography (e.g., high performance liquid chromatography). Suitable eluent solvents include, but are not limited to water, ethanol, methanol, acetone, and a mixture thereof. A gradient eluent system can be used.

Alternatively, one can also use recrystallization to acquire a pure product. The recrystallization solvent can be an inorganic or organic solvent, e.g., that in which the desired product has a low solubility at a low temperature, but has a higher solubility at a high temperature. It can also be a solvent pair or mixture.

The purities of the extract product can be determined by using chromatography or other instruments, such as NMR.

To store the thus-obtained extract product, one can place it at a low temperature, e.g., <40° or <0° C., and/or under protective gas, e.g. nitrogen, argon, or helium.

Polymeric compounds in the extract product can be further modified. More specifically, one or more substituents on the compounds can be chemically transformed in order to make other polymeric compounds that can be used to practice this invention. Chemical transformations useful in making such compounds, and chemical reagents and solvents use to perform them, are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

An effective amount of the above-obtained pharmaceutically active preparation can be used to improve liver function, treat liver fibrosis, liver cirrhosis, liver inflammation, liver infection, and liver cancer, and regenerate damaged liver tissues.

The term "improving a liver function" refers to administering the preparation to a subject, whether or not having liver disease, to enhance his or her liver's capability of metabolism, glycogen storage, decomposition of red blood cells, plasma protein synthesis, hormone production, or detoxification. The term "treating liver disease" refers to administering the preparation to a subject who has a condition of liver fibrosis, liver cirrhosis, liver inflammation, liver viral infection (e.g., hepatitis B or C virus infection), or liver cancer, or has a symptom of the condition, or has a predisposition toward the condition, with the purpose to cure, heal, alleviate, relieve, alter, remedy, ameliorate, improve, or affect the condition, the symptoms of the condition, or the predisposition toward the condition. The term "regenerating liver tissues" refers to administering the preparation to a subject whose liver has been damaged by disease, alcohol, drugs, or other causes to promote regeneration of liver tissues to reverse the liver damage. The term "an effective amount" refers to the amount of the preparation that is required to confer one of the above-described effects on the subject. The effective amount varies, as recognized by those skilled in the art, depending on the types of the effects, route of administration, excipient usage, and the possibility of co-usage with other treatment.

To practice the method of the present invention, a composition containing one or more of the polymeric compounds described above can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The effects of a compound can be tested by an in vitro or in vivo assay. For example, compounds of this invention can be preliminarily screened by in vitro assays in which the compounds are tested for their bioactivity relating to liver function. Compounds that demonstrate high efficacy in the preliminary screening can be further evaluated by in vivo methods well known in the art to evaluate their activity in treating liver conditions, e.g., liver cancer.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Preparation of Polymeric Compounds

Roots and stems of Boehmeria nivea L. Gaud. were washed with water and dried. The dried plant parts were cut into slices having a thickness of 5 mm and stored at 4° C.

Method 1:

The slices were grounded and passed through a 20-mesh sieve. The thus-obtained powder was dispersed in 95% ethanol (10 times by weight). The mixture was refluxed for 2 hours twice. After cooled to room temperature, the liquid was collected and centrifuged. The supernatant was condensed under reduced pressure at a temperature below 40° C. and freeze-dried to get a crude product.

Method 2:

The slices were grounded and passed through a 20-mesh sieve. The thus-obtained powder was dispersed in reverse osmosis water (10 times by weight). The mixture was refluxed for 2 hours twice. After cooled to room temperature, 50%-95% ethanol was added to cause precipitation. The liquid solution was collected and centrifuged. The supernatant was condensed under reduced pressure at a temperature below 40° C. and freeze-dried to obtain a crude product.

The crude products obtained from method 1 and method 2 were each dispersed in n-hexane (1:10 w/v) and refluxed using a Soxhlet apparatus for 6 hours to remove lipid. After removal of the solvent, the obtained solid was dissolved in 70% methanol-water solution and 0.3% vitamin C water solution. The solution was condensed under reduced pressure below 40° C., and then an equal volume of chloroform was added. The mixture was placed on an oscillator for 30 minutes. The water layer was separated and ethyl acetate was added. The mixture was oscillated for 30 minutes. The water layer was again separated and condensed under reduced pressure at a temperature below 40° C. and freeze-dried to give a partially purified extract.

Alternatively, the crude products obtained from method 1 and method 2 were dissolved in a mixture of water and ethanol (1:10, w/v). n-Hexane (10 times by volume) was added. The mixture was oscillated for 30 minutes to remove lipid. The water layer was separated and ethyl acetate was added. The mixture was oscillated for 30 minutes. The water layer was separated and mixed with n-butanol (1:10 v/v). After oscillation for 30 minutes, the water layer was separated, condensed under reduced pressure at a temperature below 40° C., and freeze-dried to give a partially purified extract.

2.5 g of the partially purified extract was charged onto a gel permeation chromatography column (Sephadex LH-20, 4 cm diameter×45 cm length) using different eluent solvents, including 300 mL 95% ethanol, 300 mL 95% ethanol/methanol (1/1, v/v), 300 mL methanol, 300 mL 50% methanol water solution, and 300 mL 50% acetone water solution, sequentially. The collected eluent solvents, except 95% ethanol, were condensed under reduced pressure and freeze-dried to obtain a purified extract, Sample 1, which was stored at −20° C. before use.

Characterization of Polymeric Compounds in Sample 1

Sample 1 was assessed by X-ray crystallography, NMR, and /Ionization Mass Spectrometry. Compounds of the following structures constituted at least 20% by weight of Sample 1:

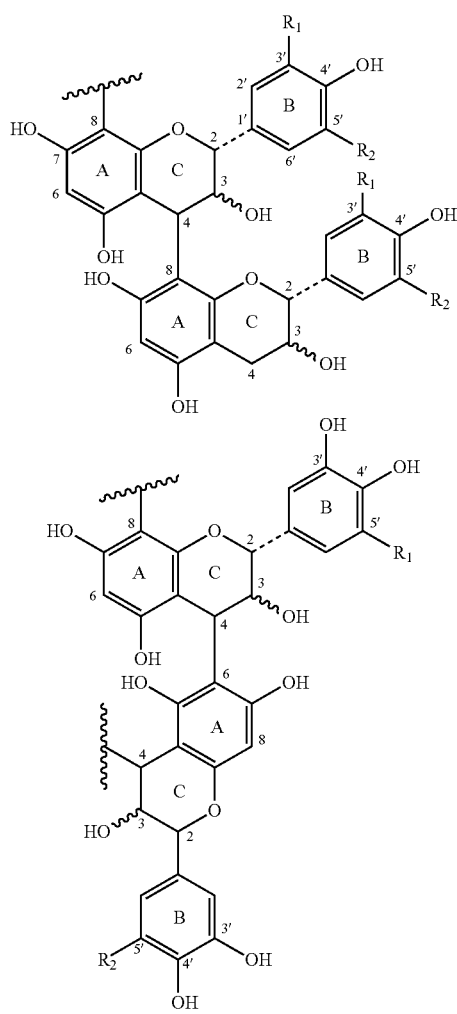

Effects of Sample 1 on Improving Liver Function

The heterozygous male hepatitis B x (HBx) gene transgenic (HBx-Tg) mouse line A112 of the C57BL/6 background was used. The mice were divided into 6 groups: (A) non-transgenic mice (wild type) mock, (B) non-transgenic mice treated with Sample 1 at the age of 9-20 months old, (C) transgenic mice mock, (D) transgenic mice treated with Sample 1 at the age of 9-20 months old, (E) transgenic mice treated with Sample 1 at the age of 12-20 months old, and (F) transgenic mice treated with Sample 1 at the age of 15-20 months old in this study. Sample 1 was dissolved in distilled water and administered p.o. (1000 mg/kg/day) to the mice using a feeding needle.

Mice were sacrificed at 20 months old. Liver tissues and sera were collected for pathologic and biochemical analysis.

Pathologic analysis: The body weight and liver weight were measured for each mouse at sacrification. The livers were collected, fixed with formalin, and embedded in paraffin. Liver sections were subjected to Hematoxylin and Eosin staining.

Alanine aminotransferase (ALT) and Aspartate aminotransferase (AST) assays: Blood samples were collected monthly. Serum ALT and AST values were analyzed by a biochemistry automated analyzer (Hitachi 7080). See Wu et al., Biochemical and Biophysical Research Communications. 2006, 340: 916-928.

The indocyanine green (ICG) retention rate test: 18 Month-old mice were injected i.v. with ICG (10 mg/di). Blood samples were collected at 10 minutes after the injection. Serum ICG retention rate was determined using a spectrophotometer at 805 nm.

Of note, ICG is a substance exclusively cleared from the blood by the liver. The ICG clearance is therefore used as an indicator to evaluate liver function. See Sheng et al., Hepatobiliary Pancreat Dis. Int. 2009, 8:46-49

The survival rate of the HBx-Tg mice (Group C) was 64% at the age of 20 months. In contrast, the survival rate of the mice treated with Sample 1 (Group E) was 100% at the age of 20 months. Thus, Sample 1 treatment increased the survival rate of HBx-Tg mice significantly. The results also show that early treatment with Sample 1 improved the survival rate of HBx-Tg mice.

The ratio of liver weight to body weight was about 5% in wild type mice (Group A), and increased to 13% in HBx-Tg mice (Group C) at age 20 months old. No significant difference in the ratio was observed between Groups A and Group B. Sample 1 treatment significantly reduced the ratio of liver weight to body weight (about 8%) in Groups D, E and F. These results indicated that Sample 1 reduced HCC progression in HBx transgenic mice.

The ICG retention rate of wild type mice (Group A) was 2.25±0.89 mg/dl, the ICG retention rate of wild type mice treated with Sample 1 (Group B) was 2.13±0.92 mg/dl. The ICG retention rate of HBx transgenic mice (4.46±1.17 mg/dl) (Group C) was significantly higher than wild type mice. The HBx-Tg mice early treated with Sample 1 (Groups D and E) significantly reduced ICG retention rate (the ICG retention rate was 2.63±0.76 mg/dl for group D and 3.47±0.77 mg/dl for Group E).

The ALT and AST were significantly increased in HBx-Tg (Group C) after the age of 12 months old. Sample 1 treatment of wildtype mice (Group B) had no any effect on ALT and AST. Sample 1 treatment of mice of HBx-Tg (Groups D and E) at different ages reduced ALT and AST significantly.

In conclusion, the results showed that Sample 1 improved liver function in the mice model.

Prevention of Liver Fibrosis

8-Week-old Wistar rats were divided into five groups: (A) Naïve group (control), (B) diethylnitrosamine (DEN) treated for 6 weeks, (C) DEN and Sample 1 treated for 6 weeks, (D) DEN treated for 9 weeks, and (E) DEN and Sample 1 treated for 9 weeks. DEN in water (100 ppm) was administered at 0.02 ml/kg/day for 6 or 9 weeks to induce liver fibrosis and hepatocellular carcinoma (HCC). The DEN solution was freshly prepared every week. Sample 1 was fed with food at a dose around 1000 mg/kg/day. The rat weights were recorded and liver tissues and sera were collected for the pathologic and biochemical analysis described below. The rats were sacrificed at $6^{th}$, $9^{th}$, or $12^{th}$ week.

Pathologic analysis: At mouse sacrifice, the livers were collected, fixed with formalin, and embedded in paraffin. Liver sections were subjected to Hematoxylin and Eosin staining and alpha-smooth muscle actin (a-SMA) immunohistochemistry staining.

Liver hydroxyproline test: 10 mg of liver samples were used to measure the amount of hydroxyproline according to the method described in Lee et al., Journal of Gastroenterology and Hepatology 2005, 20: 1109-1114.

The treatment with DEN and Sample 1 for 9 weeks at the same time (Group E) reduced the hydroxyproline amount significantly compared with treatment with only DEN rats for 9 weeks (Group D), indicating that Sample 1 prevented DEN induced liver fibrosis. Sample 1 also reduced the amount of a-SMA in the rats treated with Sample 1 for 6 weeks (Group C) and 9 weeks (Group E).

Effect on Liver Fibrosis

8-Week-old Wistar rats were treated with DEN in the manner as described above. Sample 1 (1000 mg/kg/day) mixed with food was fed to the rats during weeks 3-6, during weeks 6-9, or during weeks 9-12. Rats were sacrificed at week 12. Liver tissues were assayed in the hydroxyproline test described above.

Rats treated with Sample 1 at weeks 3-6 and 6-9 had a significantly reduced amount of hydroxyproline in liver, indicating that Sample 1 prevented or reversed the early stage of liver fibrosis.

Effect on Survival Rate of Liver Fibrotic Rats

8-Week-old Wistar rats were dived into 6 groups: (A) Naïve group, (B) DEN treated for 10.5 weeks, (C) both DEN and Sample 1 treated for 10.5 weeks, (D) DEN treated for 10.5 weeks and Sample 1 treated from weeks 3 to 10.5), (E) DEN treated for 10.5 weeks and Sample 1 treated from weeks 6 to 13.5, and (F) DEN treated for 10.5 weeks and Sample 1 treated from weeks 10.5 to 13.5. DEN in water (50 ppm) was administered at 0.01 ml/kg/day. The DEN solution was freshly prepared every week.

Sample 1 was dissolved in distilled water and administered p.o. (1000 mg/kg/day) using a feeding needle.

The animals were observed every day until 15 weeks (104 days). The survival rates were analyzed using the nonparametric statistic.

The survival rate of DEN-treated rats (Group B) was around 40%. In contrast, all Sample 1-treated rats (Groups C-F) increased survival rate by more than 80% at day 94 (13.5 weeks). These data indicated that Sample 1 increased survival rate of DEN induced HCC rats.

In addition, it was observed that Sample 1 increased the survive rate of rats of Group F not only during the Sample 1 administrating period (days 74-94) but also after the administration (days 95-99). At day 104, the survival rate of Group F was more than 60%, while the survival rate of Group B was only 40%.

In conclusion, Sample 1 increased the survival rate of DEN-induced HCC rats.

Effect on Liver Regeneration after Hepatectomy

For liver fibrosis and HCC model, 8 weeks old Wistar rats received 0.02 ml/kg/day of DEN for 9 weeks. The DEN solution was freshly prepared every week by dissolving a weekly dose of DEN in a volume corresponding to the estimated water consumption of 7 days of drinking water (100 ppm). The weights of the rats were recorded.

Sample 1 in distilled water was administered p.o. to two groups of rats (250 mg/kg/day or 1,000 mg/kg/day) using a feeding needle at weeks 6-9. 70% of liver was removed by hepatectomy at week 9. The regenerated liver tissues were collected 2 days after the hepatectomy. The cell mitosis ability of liver sections with Hematoxylin and Eosin staining was analyzed.

The mitosis rate of the liver treated with DEN and hepatectomy (7.6±4.6) was lower than both Sample 1-treated groups (12±5.5). These data indicated that Sample 1 promoted damaged liver regeneration.

8 Weeks old Wistar rats were treated with DEN or DEN and Sample 1 (50 mg/kg/day and 1,000 mg/kg/day) in the same manner as described above. 30% of liver was removed by hepatectomy at week 9. The liver mass was measured by magnetic resonance imaging (MRI) 2 weeks before and 2 weeks after hepatectomy. The rats were sacrificed at week 11.

The liver regeneration rate in the Sample 1-treated groups was significantly increased compared with that of the DEN group (79±6% vs. 32±7%). Reduced food consumption was observed in the DEN group (42±5%) 2 days after hepatectomy, but treatment with SAMPLE 1 recovered the food consumption (83±4%) to the level similar to that of the naïve group (91±3%). Food uptake time was longer in the DEN-treated group (27.0±3.3 hrs) compared to the naïve group (11.0±1.2 hrs) 2 days after hepatectomy. Treatment with Sample 1 reduced food uptake time to 16.0±2.4 hrs.

The Sample 1-treated groups had a survival rate of 100%, while the DEN group had a survival rate of 55% after hepatectomy.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of regenerating liver tissues, comprising administering to a subject in need thereof a pharmaceutical composition, the pharmaceutical composition being obtained by (a) mixing a pharmaceutically acceptable carrier and (b) an isolated preparation that contains one or more polymeric compounds, each of which includes two or more monomer units having the following formula:

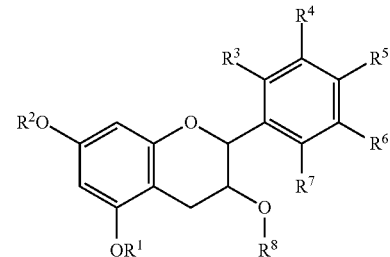

in which each of $R^1$ and $R^2$ independently, is H, alkyl, or acyl; each of $R^3$, $R^4$, $R^5$, $R^6$, and $R^7$, independently, is H, OH, alkoxyl, or acyl; and $R^8$ is H or a saccharide moiety;

wherein the polymeric compounds constitute 20% or higher of the isolated preparation by weight.

2. The method of claim 1, wherein $R^1$ and $R^2$, independently, is H.

3. The method of claim 2, wherein each of $R^3$ and $R^7$ is H.

4. The method of claim 3, wherein each of $R^4$, $R^5$, and $R^6$ is OH or alkoxyl.

5. The method of claim 4, wherein $R^8$ is H.

6. The method of claim 5, wherein the polymeric compound includes 2-30 monomer units.

7. The method of claim 6, wherein the monomer units are covalently bonded to each other via C4-C8 bonding, C4-C6 bonding, or C2-O7 bonding.

8. The method of claim 1, wherein the polymeric compound includes 2-30 monomer units.

9. The method of claim 8, wherein the monomer units are covalently bonded to each other via C4-C8 bonding, C4-C6 bonding, or C2-O7 bonding.

10. The method of claim 1, wherein each of $R^4$, $R^5$, and $R^6$ is OH or alkoxyl.

11. The method of claim 1, wherein the subject received hepatectomy.

* * * * *